United States Patent [19]
Legay

[11] Patent Number: 5,836,980
[45] Date of Patent: Nov. 17, 1998

[54] METHODS AND APPARATUS FOR DISCRIMINATING CHARACTERISTIC SIGNALS FROM PARASITIC SIGNALS IN ACTIVE IMPLANTABLE MEDICAL DEVICES

[75] Inventor: Thierry Legay, Fontenay Les Brilis, France

[73] Assignee: ELA Medical S.A., Montrouge, France

[21] Appl. No.: 755,335

[22] Filed: Nov. 22, 1996

[30] Foreign Application Priority Data

Nov. 22, 1995 [FR] France ................... 95 13831

[51] Int. Cl.⁶ .................................................. A61N 1/362
[52] U.S. Cl. ................................................. 607/9; 128/901
[58] Field of Search ............... 607/9, 26; 128/901, 128/696; 600/509

[56] References Cited

U.S. PATENT DOCUMENTS

| 3,848,586 | 11/1974 | Suzuki et al. ................. 128/901 |
| 4,516,579 | 5/1985 | Irnich . |
| 4,537,201 | 8/1985 | Delle-Vodove et al. . |
| 5,339,820 | 8/1994 | Henry et al. . |
| 5,370,124 | 12/1994 | Dissing et al. . |
| 5,456,263 | 10/1995 | Andersen ........................... 607/26 |

FOREIGN PATENT DOCUMENTS

| 105784A1 | 4/1984 | European Pat. Off. ......... A61N 1/36 |
| 321764A1 | 6/1989 | European Pat. Off. ......... A61N 1/37 |
| 549438A1 | 6/1993 | European Pat. Off. ......... A61N 1/08 |
| 580894A1 | 2/1994 | European Pat. Off. ......... A61N 1/37 |
| 3232478A1 | 3/1984 | Germany ........................ A61N 1/36 |

*Primary Examiner*—William E. Kamm
*Assistant Examiner*—George R. Evanisko
*Attorney, Agent, or Firm*—Orrick, Herrington & Sutcliffe, LLP

[57] ABSTRACT

A circuit and process for an active implantable medical device, particularly a cardiac type pacemaker or defibrillator of the "demand" type, for discrimination between parasitic signals and characteristic signals. Such a device includes a detection circuit (10) to collect a cardiac signal (SA), which may be a spontaneous or stimulated cardiac signal, of the bearer of the device. The collected cardiac signal includes a characteristic signal component and undesirable parasitic signal component. The device also includes a discriminating circuit (12–18) and technique for receiving as an input the collected cardiac signal and delivering at an output a signal (ST) desirably corresponding essentially to the characteristic signal, from which any parasitic signals have been removed. The discrimination circuit and technique include a differentiating circuit (14) to provide successive values of the slope of the actual collected cardiac signal, and a comparator circuit (18) to compare the slope values to a reference discriminating slope values to remove parasitic signals from the collected cardiac signals. In the case that the variation thus evaluated is in a range between predetermined negative and positive limits, the variation is left unchanged. In the opposite case, the cardiac signal variation is limited to a predetermined value, respectively positive (PSC) or negative (PSD). Thus, the limited variation follows the actual cardiac signal, and by subtracting the processed signal (which is limited or nonlimited) from the actual signal, the difference yields the characteristic signals.

24 Claims, 3 Drawing Sheets

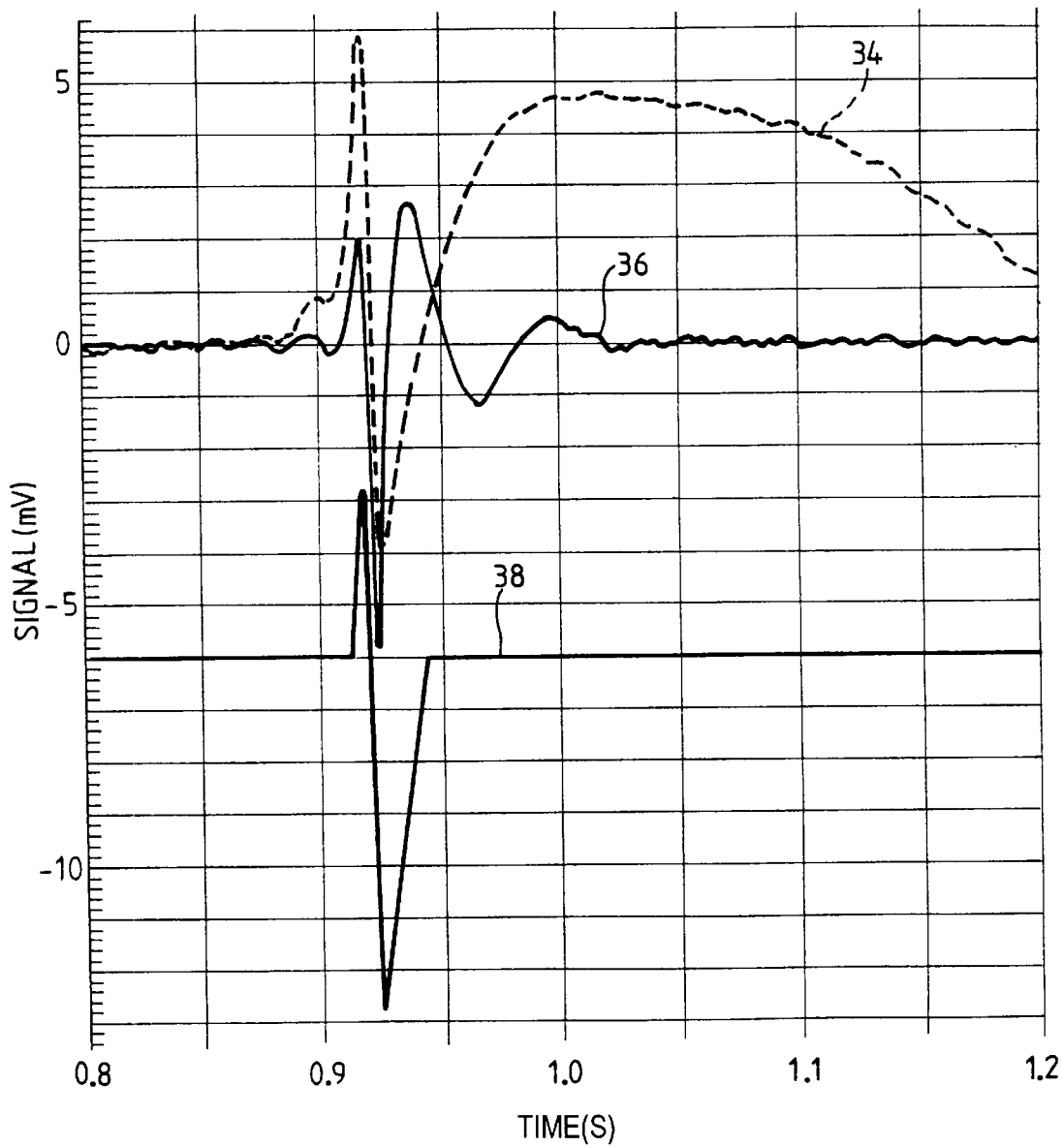

METHODS AND APPARATUS FOR DISCRIMINATING CHARACTERISTIC SIGNALS FROM PARASITIC SIGNALS IN ACTIVE IMPLANTABLE MEDICAL DEVICES

FIELD OF THE INVENTION

The present invention concerns "active implantable medical devices" such as are defined by the Jun. 20, 1990, Directive 90/385/EEC of the European Community Council, and more particularly cardiac pacemakers and/or defibrillators of the "demand" type, whose functioning depends on the detection of a cardiac signal spontaneously produced by the heart of a patient bearing the device.

BACKGROUND OF THE INVENTION

When spontaneous cardiac activity is effectively detected, and if some other conditions are fulfilled, the demand device can inhibit the delivery of a stimulation pulse. In a more general manner, a demand device can adapt its behavior to the detected spontaneous cardiac signals so that its behavior respects the physiology of the patient. This is desirable because one wants not to interfere with normal physiology, and the demand device thus minimizes the risk of delivering to the patient unnecessary stimulation pulses or other therapy.

It is, however, necessary, among the signals collected (that is, in the sensed or detected cardiac signals, which terms are used interchangeably), to discriminate the "characteristic signals" from the "parasitic signals." The "characteristic signals" are those that actually correspond to spontaneous cardiac activity signals and are used therefore to command the adaptation of the behavior of, for example, the pacemaker. The "parasitic signals" are other signals, such as electronic or cellular noise or cardiac activity, that are not to be used for control purposes, and become mixed in with the characteristic signals and are collected at the same time as the characteristic signals.

The discrimination between characteristic signals and parasitic signals depends in part on the cardiac cavity in which the detection is operated. In the atrium, the atrial characteristic signals are P-waves, atrial fibrillation or atrial extrasystoles. The variations of amplitude of these characteristic signals can be large in a given patient. The atrial characteristic signals thus have to be distinguished from atrial parasitic signals, such as signals arising from damaged tissue (lesions) and signals of the repolarization of the heart-electrode interface after a stimulation. When the detection is operated in the ventricle, the ventricular characteristic signals are R-waves, ventricular fibrillation and ventricular extrasystoles. The ventricular characteristic signals thus have to be distinguished from ventricular parasitic signals such as T-waves, lesion signals and signals of the repolarization of heart-electrode interface after a stimulation.

If the discrimination is not suitably performed, it can result in a "loss of detection" or a "false detection," which effects have been largely described in the literature. One result can be improper stimulation (delivery or no delivery) with a resultant risk of induced dizziness for the bearer of the device.

Present cardiac pacemakers (or defibrillators) are virtually all of the aforementioned "demand" type, and possess therefore some means to discriminate spontaneous "characteristic" cardiac signals from "parasitic" cardiac signals. The discrimination is generally performed by filtering detected signals in the frequency domain. Typically, the intra-cardiac signal is processed through a high-pass filter with a cut-off frequency somewhere between 10 and 30 Hz. This provides for attenuating the aforementioned parasitic signals, whose frequency spectrum typically spreads below than that of the characteristic signals which pass through the high-pass filter.

This technique, although safe and effective, nevertheless presents several disadvantages. One is that the value of the frequency that allows one to separate optimally the two respective spectral areas of parasitic and characteristic signals can vary from patient to patient. This necessitates therefore, if the pacemaker allows it, a particular adjustment after analysis of the specificity of the cardiac rhythm of the given patient.

Another difficulty is that even if the frequency value is optimized according to the patient, parasitic signals still have a residual component (e.g., a harmonic) in the passed frequency band, which residual component can be disturbing when the characteristic signal level is very low. In addition, due to the high-pass filtering, useful characteristic signals are partially attenuated, which renders their detection more difficult.

Indeed, a very pure signal that would comprise only characteristic signals, for example, in the case of a ventricular detection, only R-wave signals spontaneously emitted by the heart of the patient according to its own rhythm, for example, at 60 pulses per minute, possesses a major part of its spectral energy in the low frequency domain, i.e., in the frequency domain situated below 30 Hz. Consequently, by filtering this domain, a significant part of the useful energy of the signal is lost.

OBJECTS AND SUMMARY OF THE INVENTION

It is, therefore, an object of the present invention to remedy these noted various disadvantages by proposing a process of and an apparatus for discrimination based on a technique other than high-pass filtering.

It should be understood that the present invention applies to an active implantable medical device of the aforementioned type, that is to say having well-known and conventional detector circuits for collecting the spontaneous or stimulated cardiac signal of the bearer of the device, which collected cardiac signal comprises a characteristic signal component and components of undesirable parasitic signals, and a means for discriminating these signals, receiving as an input the collected cardiac signal, and delivering as an output a signal corresponding to the characteristic signal from which parasitic signals have been removed.

In accordance with the present invention, discrimination of the characteristic and parasitic signals is obtained by evaluating successive variations of the collected cardiac signal and comparing the variations to a predetermined limit. By limiting the variation to a predetermined limit when the variation satisfies certain conditions, the parasitic signals can be effectively removed from the collected cardiac signals leaving substantially the characteristic signals.

One aspect of the invention is directed to an apparatus, more specifically a discriminating means which comprises a differentiation circuit that delivers successive slope values of the collected cardiac signal, and a circuit that compares these slope values to a reference slope value.

Another aspect of the invention is directed to a method for processing the collected cardiac signal, which method includes differentiating the collected cardiac signal to determine a slope value, and comparing the determined slope value to a reference slope value. The comparison is then used to discriminate the parasitic signals from the characteristic signals and suppress the parasitic signals, based on noting when the variation satisfies certain conditions and limiting the variation in those conditions.

In one embodiment of the apparatus, the detector circuit comprises a means for sampling and digitizing the detected cardiac signal in a conventional manner, and the differentiation circuit establishes successive slope values of the cardiac signal samples by determining an increment between two successive cardiac signal samples.

In one variation of this embodiment, the differentiation circuit also operates as a limiting means to subtract from the actual digital signal sample a preceding digital value which may have been limited, as will be described, and to compare the absolute value of the resulting difference to a predetermined discriminating slope value. In this case, when the absolute value of the resulting difference is greater than the discriminating slope value, the limiting means adds or subtracts, according to whether the slope is increasing or decreasing, to the preceding limited digital value, a given increment. The increment is equal to a negative predetermined limit value in the case of a decreasing slope and a positive predetermined limit value in the case of an increasing slope. The limiting means then delivers as an output a corresponding limited digital signal value which represents the parasitic signal value extracted from the actual collected cardiac digital signal. If the absolute value of the aforementioned resulting difference is not greater than the discriminating slope value, then the limiting means does not limit the actual value, but sets the limited digital signal value equal to the actual digital signal value. Each limited digital signal (whether or not actually limited) then becomes the preceding limited signal for evaluation of the slope of the next cardiac signal sample. The limited digital signals thus are the extracted parasitic signals, which will then be subtracted, sample by sample, from the actual collected cardiac digital signals to produce processed signals containing only the characteristic signals.

The discriminating slope value is preferably an adjustable value, especially according to a function of the collected cardiac signal as the latter evolves, but could be a programmable value. Further, the positive limit and/or the negative limit of the limiting means, and/or the value of reference discriminating slope value, are preferably adjustable values, particularly according to a function of the collected cardiac signal as it evolves but could be a programmable value or values.

In addition, the positive limits and/or the negative limits of the limiting means are preferably related to the value of the reference discriminatory slope value.

In addition, the variations in the collected cardiac signal may be compared relative to a predetermined range between a positive value and a negative value.

The collected cardiac signals can be collected over time, a slope value for each collected cardiac signal determined, and the determined slope compared to a discriminating slope range, such that a determined slope value being outside the range is limited. The range is defined by predetermined negative and positive limits. In a preferred embodiment, the comparison of the determined slope to the discriminating slope range includes taking an absolute value of the difference between successive collected cardiac signals and comparing it to a discriminating slope value. The sign of the absolute value exceeding the discriminating slope value can be determined to apply an appropriate positive slope limit or negative slope limit, depending on whether the slope is increasing or decreasing.

BRIEF DESCRIPTION OF THE DRAWINGS

Other characteristics and advantages of the present invention will appear to a person of ordinary skill in the art in view of the following detailed discussion, made with reference to the drawings annexed, in which:

FIG. 3 is a graphical illustration plotted in amplitude (mV) versus time (seconds), of a collected cardiac signal, the result of a classic discrimination circuit of the prior art high-pass filter type, and the result of a discrimination circuit according to the present invention.

DETAILED DESCRIPTION OF THE DRAWINGS

Figure 1:
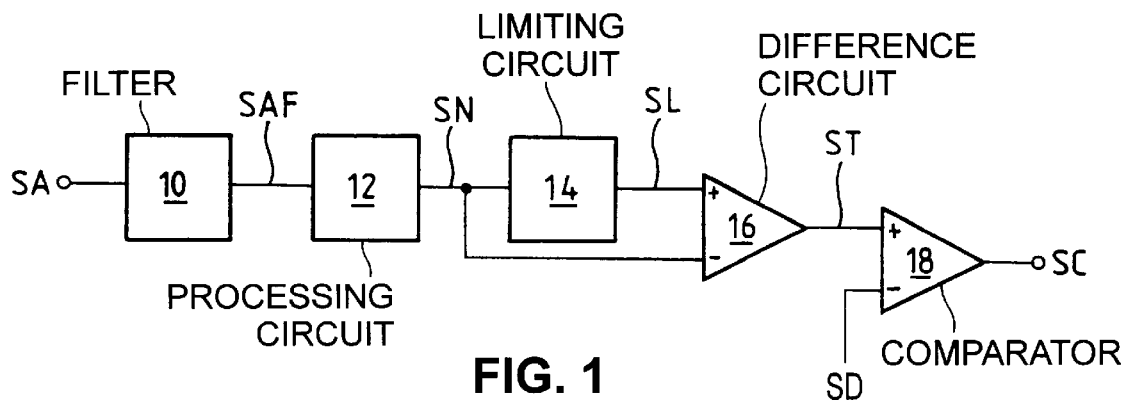
FIG. 1 is a block diagram representation of an implementation of the structure and function in accordance with a preferred embodiment of the invention.

Referring to FIG. 1, the principle implemented by the invention is represented schematically in the form of a functional block diagram. The basic idea of the invention is not to use filtering of the collected signal in the frequency domain, but, rather, to follow the higher slopes of the cardiac signal to discriminate the parasitic signals. The slope is defined as the first derivative of the collected signal. The derivative can be satisfactorily approximated, in the case of a sampled signal, by the value of the increase of the signal during a duration of a predetermined fixed time, typically the duration separating the determination of the values of two successive samples.

The invention is a result of an observation of the existence of a slope limit or a discriminating slope PD that can be used to distinguish characteristic signals from parasitic signals. As realized by the inventor, the characteristic signals have slopes that are notably greater than the slopes of parasitic signals. This has the result that processing the signal by analysis of its slope allows to detect the presence or the absence of a characteristic signal, and therefore to command or not a particular action of the device, for example, the inhibition of the stimulation in a pacemaker.

Referring to FIG. 1, the analog cardiac signal SA collected by the endocardial electrode (not shown) is first of all pre-processed by a filter circuit 10. Filter 10 is a preconditioning filter, such as a low-pass filter, to eliminate all signals situated above a given frequency, for example, 500 Hz, beyond which spectrum one does not find characteristic signals. Such filtering is conventional in the art, and may be performed digitally or by analog circuits.

The resulting filtered analog signal SAF is then submitted to the process according to the invention, which can be realized either in an analog form, or in a digital form, e.g., by software.

In its simplest form, the filtered analog signal SAF is applied to a circuit 12 for converting the analog signal to a digital signal and for obtaining the derivative of the signal. Circuit 12 delivers the digital signal SN. The sampling of the signal SAF is preferably performed at a frequency compatible with the spectral band, therefore, a frequency of at least twice the high cut-off frequency of the low-pass filter circuit 10.

The digital signal SN then undergoes, by a limit circuit 14, a limitation of slope in certain conditions, in the positive value as well as in the negative value, thus providing a limited slope signal referred to as limited signal SL. A manner in which one can realize this limitation of slope is described below. Although referred to as a limited signal, it actually may include both limited samples and non-limited samples, as will become clear in the following discussion.

In a circuit 16, the limited signal SL is subtracted from the digital signal SN to give a processed signal ST containing only the characteristic signals. The amplitude of processed signal ST can then be compared, in a circuit 18, to a threshold, SD. One obtains thus a command signal SC corresponding essentially to the detection of the characteristic signal, that is the digital signal SN from which the parasitic signals have been removed, relative to the threshold SD. The threshold SD can be a detection threshold fixed as low as necessary, because only characteristic signals are present in the processed signal ST. As a result, the sensitivity and specificity of the device are substantially increased.

Another advantage of the invention is to allow the modification of the processing operation by modifying some quantitative parameters, such as the limits in the circuit 14 or the threshold PD. The modification can be either on command, or by an entirely automatic manner. In the latter case, one realizes an auto-adaptation of the circuit in relation with the characteristics of the digital input signal SN, particularly the average amplitude of the input signal SN. The change on command may be by, for example, reprogramming a value stored in a memory register in a microprocessor, digital circuit, or analog circuit based device.

Figure 2:
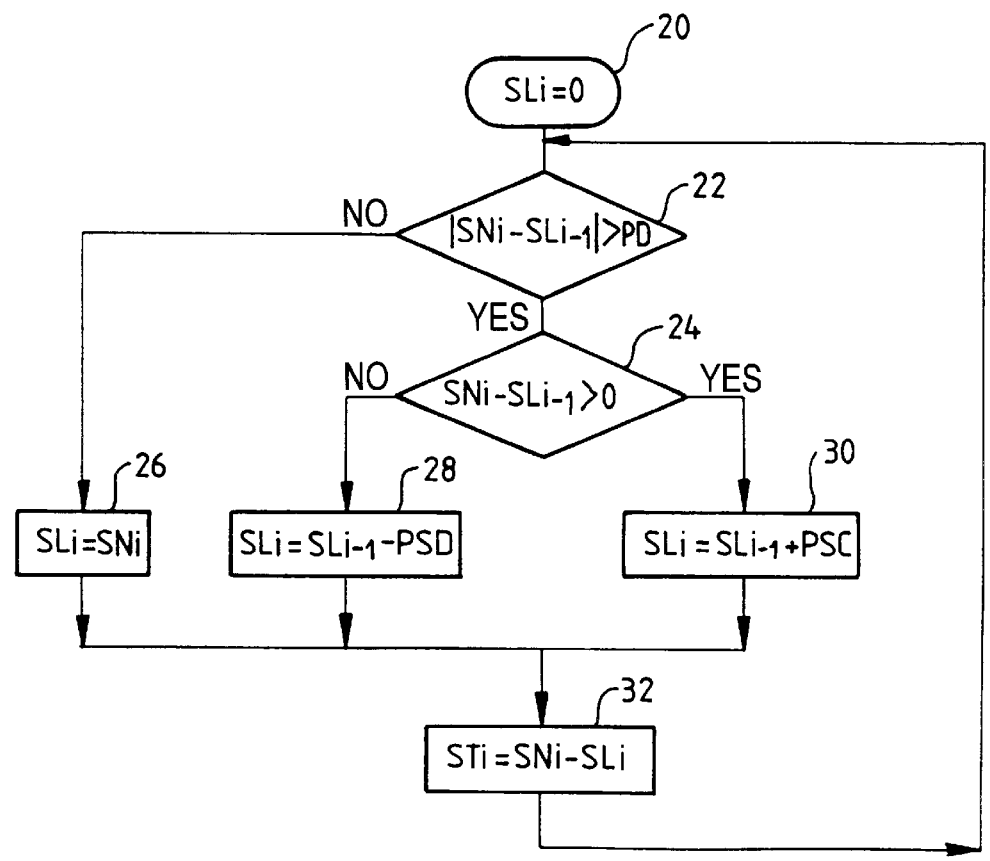
FIG. 2 is a flow chart illustrating cardiac signal processing of FIG. 1 (stages 14 and 16) according to the invention realized in a software implementation.

A software form of the implementation of the invention will now be described, with reference to the flow chart of FIG. 2. Stages 20 to 30 serve to produce the actual limited signal SLi (that is, the value of limited signal SL at instant i) from the sample value of the digital signal sample SNi, to obtain the processed signal STi. As used herein, "i" refers to a given instant and "i-1" corresponds to the preceding instant, such that "i-1" and "i" correspond to the instants of successive samples.

After the stage of initialization 20, where the value SLi is reset to zero, the stage 22 compares the actual digital signal sample SNi to the preceding limited signal sample value SLi-1 and one examines if, in absolute value, their difference is strictly greater than the discriminating slope value PD.

If the test is negative, then the slope of the variation of the signal is less than the discriminating slope value PD and the limited signal undergoes no modification. In this case, at stage 26, the limited signal sample SLi takes the value of the digital signal sample SNi, such that it follows therefore the collected signal SN exactly. In the opposite case, this indicates that the digital signal sample SNi has varied very fast, and the limited signal value SL is going therefore to follow the digital signal only after a limitation of the value by applying increasing or decreasing slope values PSC and PSD, as appropriate.

The test at stage 24 then determines if the signal sample values are increasing or decreasing, that is, the sign of the slope. In case of a decrease (stage 28) the limited signal value SLi is set equal to its preceding limited signal value SLi-1 decreased by the limit value PSD, corresponding to the decreasing slope limit. In case of an identified increase (stage 30), the actual limited signal value SLi is set to its preceding limited signal value SLi-1 increased by the limit value PSC, corresponding to the increasing slope limit.

Finally, at stage 32, the value of the actual processed signal STi is calculated simply as the difference between the value of the digital signal SNi and the value set for the limited signal SLi.

One will note that, in the case of a negative test at stage 22, the difference thus calculated at stage 32 is zero (null). If the digital signal sample has a lower slope in comparison to the discriminating slope value PD, then the value of the processed signal ST at stage 32 will be zero (null). Therefore, if one chooses in a judicious manner the value PD, parasitic signals of low slope, that is, relatively slowly varying signals, will be totally eliminated from the processed signal ST, and not simply attenuated as would occur in the case of filtering.

Concerning the increasing slope limit PSC and the decreasing slope limit PSD, they will have to be chosen sufficiently low in order not to attenuate too much rapid characteristic signals, but not too low because they condition in fact the response time for the processed signal to follow the digital signal in case of divergence, particularly at the initialization phase.

Thus, one can, for example, render equal the slope limits PSC and PSD, and to index these values on the discriminating slope value, by taking, for example, PSC=PSD=PD/4. Concerning the choice of the value of the discriminating slope value PD, it can result from a statistical study that is empirically derived. A suitable value PD is a coefficient of 50 mV/s times the millivolt level of cardiac characteristic signal (e.g., R-wave or P-wave), which allows a good identification of parasitic signals for their subsequent rejection. As noted, in an auto-adaptation embodiment, the coefficient can be times an average millivolt level of the cardiac signal.

Figure 2A:
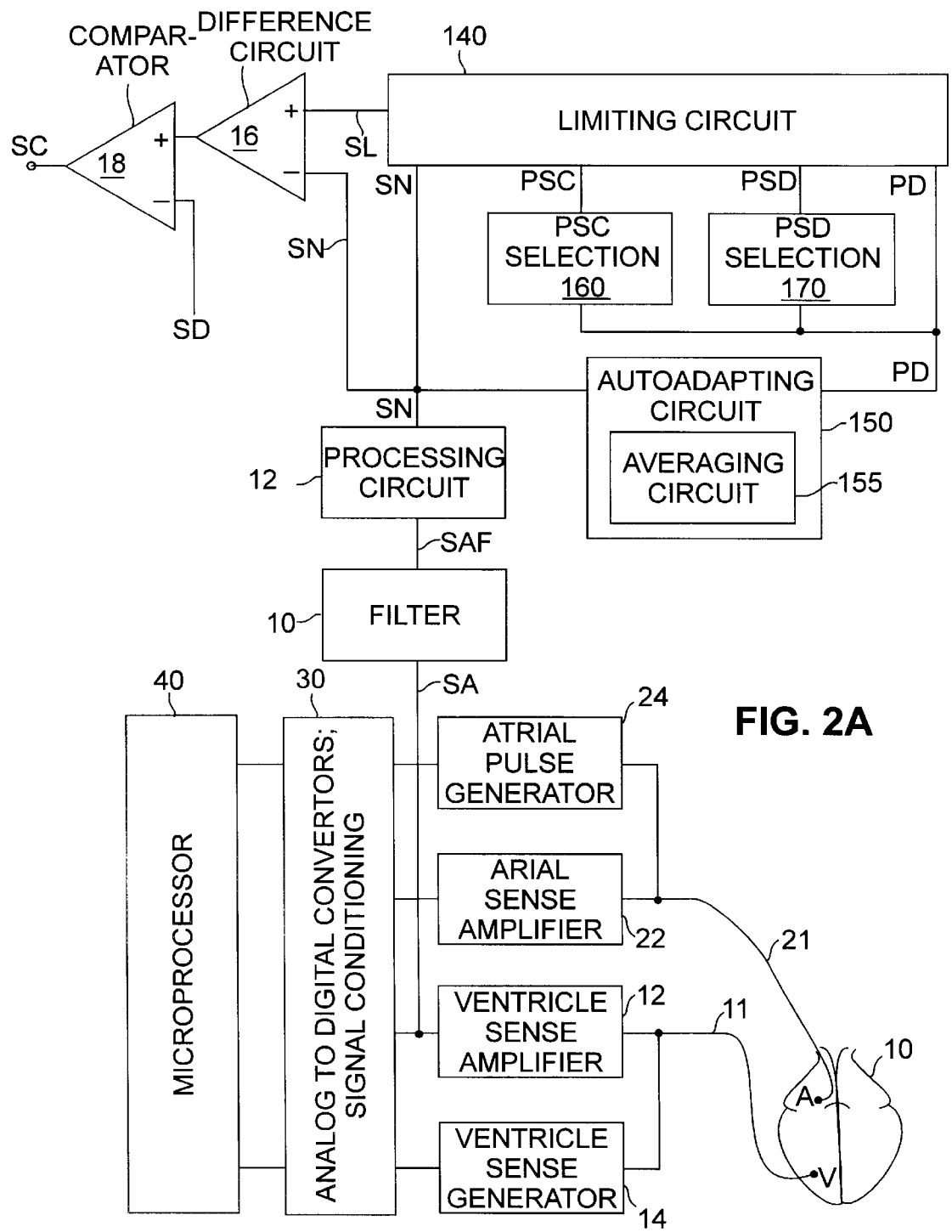
FIG. 2A is a block diagram representation of an alternate implementation of the invention of FIG. 1 in a dual chamber pacemaker.

FIG. 2A shows a dual chamber pacemaker 100 having an atrial pulse generator 124 and an atrial sensing amplifier 122, a ventricular pulse generator 114 and a ventricular sense amplifier 112, an analog to digital conversion and conditioning circuit 130 and a microprocessor 140, all of which are in themselves well known and which need not be described in detail here. In this embodiment, the present invention is implemented by coupling the circuit of FIG. 1 to the output SA of the ventricular sense amplifier 112 (which circuit may be implemented within conditioning circuits 130 although shown separately for clarity of presentation).

In the embodiment shown in FIG. 2A, the device includes an autoadaption circuit 150, which is connected to the collected ventricular signal SN, and outputs the signal PD as a function of the collected cardiac signals SN. Selection circuits 160 and 170 respectively receive the signal PD and in turn output signals PSC and PSD as a function of the input signal PD. Preferably, autoadaption circuit 150 includes an average circuit 155 which produces an output PD which is an average of the input signal SN, and circuits 160 and 170 respectively divide signal PD by four to produce signals PSC and PSD.

Alternatively, the signals PSC at PSC could be derived by selection circuits 160 and 170 as a function of the autoadaption circuit 150 output, and signal PD in turn derived as a function of the output of circuit 160 or 170, as the case may be.

In yet another embodiment, the circuits depicted in FIG. 2A could be implemented as software instructions in the microprocessor 140.

FIG. 3 shows graphically an example of an obtained comparative test results over a time according to the present invention. The reference 34 illustrates a collected spontaneous ventricular cardiac signal in voltage versus time, with a signal R (characteristic signal R-wave) and a signal T (parasitic signal T-wave).

Reference 36 illustrates the signal obtained by a classic high-pass filtering at 16 Hz (a Tchebyscheff filter of third order, undulation 0.1 dB). This result is compared to the signal 38 obtained by the implementation of the invention, where one sees clearly that this signal comprises only the complex R characteristic signal. That is precisely what the device seeks to detect. In this example, the discriminating slope value used is 0.45 V/s, the R-wave amplitude being in the range of 10 mV. In this example, PCS=PSD=PD/4.

The parasitic signal constituted by the signal T, as well as the light noise also observed on the input signal 34 leave no residual component, as compared to the signal 36 simply filtered in accordance with the known prior art. The moderated amplitude of noise is effectively eliminated due to the fact that it presents a lower slope in comparison to the discriminating slope value.

Finally, one will note that the amplitude of the signal R is less attenuated by the processing of the invention than by the filtering, which allows the device to be able to detect this signal by placing the threshold of detection at a very low level, for example, 0.4 mV, without fearing a false detection. This improves the sensitivity and reliability of the device.

It should be understood that the present invention can be implemented using a hardware architecture that includes a microprocessor executing instructions from a memory, and having analog and/or digital circuits, in themselves known. Such a microprocessor based architecture is employed in the CHORUS model series of pacemakers manufactured by ELA Medical, of Montrouge France, and in the DEFENDER model series of defibrillators, also manufactured by ELA Medical, all of which may be adapted by a person of skill in the art to implement the present invention by reprogramming of the software. The cardiac signal collecting circuits, low-pass filtering (preconditioning) circuits and digitizing circuits may be of any type, are generally well-known, and therefore are not described herein.

One skilled in the art will appreciate that the present invention can be practiced by other than the described embodiments and algorithm, for example, by digital and/or analog discrete circuits, which embodiments and algorithm are presented for purposes of illustration and not of limitation.

I claim:

1. An active implantable medical device comprising;
    a detector to collect a cardiac signal (SA), said collected cardiac signal comprising a characteristic signal component and a parasitic signal component, in which the detector further comprises an analog to digital converter having as an input the collected cardiac signal, and having as an output a digital cardiac signal comprising successive samples corresponding to said collected cardiac signals and
    a discriminating means for receiving as an input the collected cardiac signal and delivering as an output a signal (ST) corresponding essentially to the characteristic wherein the discriminating means further comprises:
        a differentiating and limiting means for evaluating the cardiac signal for variations in said cardiac signal relative to a predetermined discriminating range, said range being between a positive value and a negative value, and for limiting, in response to a variation being outside said predetermined discriminating range, said variation to a predetermined limit, said predetermined limit being one of a positive limit value for variations greater than the positive value and a negative limit value for variations less than said negative value, the differentiating and limiting means further comprising:
        means for determining an increment between two successive digital cardiac signal samples (SNi, SLi-1) as said variation; and
        means for establishing successive slope values of the digital cardiac signal samples by evaluation of said increment,
        means for subtracting from each digital signal sample (SNi) the preceding limited digital cardiac signal sample (SLi-1), and
        means for taking an absolute value of the resulting difference and comparing the absolute to a predetermined discriminating slope value (PD); and
    first means for adjusting the discriminating slope value (PD) as a function of the collected cardiac signal.

2. The device of claim 1, further comprising means for determining if the absolute value of the resulting difference is greater than the predetermined discriminating slope value (PD), and the differentiating and limiting means further comprises means for adding to the preceding limited digital cardiac signal value (SLi-1) said predetermined positive limit value in response to the resulting difference being greater than zero, means for subtracting from the preceding limited digital cardiac signal said predetermined negative limit value in response to the resulting difference being less than zero, and means for delivering at the output a corresponding variation limited value (SLi).

3. The device of claim 1, further comprising second means for adjusting the predetermined positive limit value and the predetermined negative limit value as a function of the collected cardiac signal.

4. The device of claim 3 wherein, in absolute value, the predetermined positive limit value is equal to a fraction of said discriminating slope value (PD).

5. The device of claim 1, further comprising means for adjusting the predetermined positive limit value and the predetermined negative limit value as a function of the collected cardiac signal.

6. A method for processing collected cardiac signals used in an active implantable medical device comprising:
    a) collecting cardiac signals of a patient, said cardiac signals having a characteristic signal component and a parasitic signal component;
    b) obtaining a plurality of sample values of the collected cardiac signal over a time;
    c) determining a slope for each collected cardiac signal sample;
    d) comparing each determined slope to a discriminating slope range, and:
        i) in response to the determined slope being outside the discriminating slope range, applying a slope limit to said cardiac signal sample and reducing the cardiac signal sample value according to a slope limit and a preceding cardiac signal value, and providing an output sample value corresponding to the reduced collected cardiac signal value; and
        ii) in response to the determined slope value being inside the discriminating slope range, providing an output sample value corresponding to the collected cardiac signal sample, wherein said output sample values over said time correspond to the characteristic signal component; and e) adjusting said slope limit as a function of the collected cardiac signals.

7. The method of claim 6 wherein:
step (b) further comprises digitizing the collected cardiac signals;
step (c) further comprises obtaining a digital sample (SNi) to be evaluated and a preceding limited signal digital sample (SLi-1), and subtracting the preceding limited digital sample (SLi-1) from said digital sample (SNi); and
step (d) further comprises comparing an absolute value of said difference to a discriminating slope value (PD) and providing an output signal sample value (SLi).

8. The method of claim 7 wherein step (d)(i) further comprises:
determining whether the slope is increasing or decreasing;
in response to an increasing slope, reducing the digital sample (SNi) to the preceding limited digital value (SLi-1) incremented by a positive slope limit (PSC); and
in response to a decreasing slope, reducing the digital sample (SNi) to the preceding limited digital sample (SLi-1) decremented by a negative slope limit (PSD).

9. The method of claim 8 further comprising providing the positive slope limit as equal to a fraction of the predetermined discrimination slope value.

10. An implantable cardiac pacemaker having a means for collecting cardiac activity signals and a means for processing the collected cardiac activity signals according to the method of claim 6.

11. A method for processing collected cardiac signals used in an active implantable medical device comprising:
a) collecting cardiac signals of a patient, said cardiac signals having a characteristic signal component and a parasitic signal component;
b) obtaining a plurality of sample values of the collected cardiac signal over a time;
c) determining a slope for each collected cardiac signal sample;
d) determining whether the slope is increasing or decreasing;
e) comparing each determined slope to a discriminating slope range, and:
 i) in response to the determined slope being outside the discriminating slope range, applying a slope limit to said cardiac signal sample and reducing the cardiac signal sample value according to a slope limit and a preceding cardiac signal value, and providing an output sample value corresponding to the reduced collected cardiac signal value; and
 ii) in response to the determined slope value being inside the slope discriminating range, providing an output sample value corresponding to the collected cardiac signal sample,
wherein said output sample values over said time correspond to the characteristic signal component, and
in response to an increasing slope, reducing the cardiac signals sample to the preceding reduced collected cardiac signal value incremented by a positive slope limit; and
in response to a decreasing slope, reducing the cardiac signal sample to the preceding reduced collected cardiac signal sample decremented by a negative slope limit,
(f) adjusting said slope limit as a function of the collected cardiac signals.

12. The method of claim 11 wherein:
step (b) further comprises digitizing the collected cardiac signals;
step (c) further comprises obtaining a digital sample (SNi) to be evaluated and a preceding limited signal digital sample (SLi-1), and subtracting the preceding limited digital sample (SLi-1) from said digital sample (SNi); and
step (e) further comprises comparing an absolute value of said difference to a discriminating slope value (PD) and providing an output signal sample value (SLi).

13. The method of claim 11 further comprising providing the positive slope limit as equal to a fraction of the predetermined discrimination slope value.

14. An implantable cardiac pacemaker having a means for collecting cardiac activity signals and a means for processing the collected cardiac activity signals according to the method of claim 11.

15. A method for processing collected cardiac signals used in an active implantable medical device comprising:
a) collecting cardiac signals of a patient, said cardiac signals having a characteristic signal component and a parasitic signal component'
b) obtaining a plurality of sample values of the collected cardiac signal over a time;
c) determining a slope for each collected cardiac signal;
d) providing a slope limit;
e) comparing determined slope to a discriminating slope range and:
 i) in response to the determined slope being outside the discriminating slope range, applying the slope limit to said cardiac sample and reducing the cardiac signal sample value according to the slope limit and a preceding cardiac signal value, and providing an output sample value corresponding to the reduced collected signal value; and
 ii) in response to the determined slope value being inside the discriminating slope range, providing an output sample value corresponding to the collected cardiac signal sample;
wherein said output sample values over said time correspond to the characteristic signal component, and the slope limit value is equal to a fraction of the predetermined discrimination slope range,
(f) adjusting said slope limit as a function of the collected cardiac signals.

16. The method of claim 15 wherein:
step (b) further comprises digitizing the collected cardiac signals;
step (c) further comprises obtaining a digital sample (SNi) to be evaluated and a preceding limited signal digital sample (SLi-1), and subtracting the preceding limited digital sample (SLi-1) from said digital sample (SNi); and
step (e) further comprises comparing an absolute value of said difference to a discriminating slope value (PD) and providing an output signal sample value (SLi).

17. An implantable cardiac pacemaker having a means for collecting cardiac activity signals and a means for processing the collected cardiac activity signals according to the method of claim 15.

18. An active implantable medical device comprising:
a detector to collect a cardiac signal, said collected cardiac signal comprising a characteristic signal component and a parasitic signal component, and a discriminating means for receiving as an input the collected cardiac signal and delivering as an output a signal corresponding essentially to the characteristic signal, wherein the discriminating means further comprises:

a differentiating and limiting means for differentiating the cardiac signals, evaluating the differentiated cardiac signal for variations in said cardiac signal relative to a discriminating slope value and determining whether the slope is positive or negative, and for limiting, in response to a variation being greater than said discriminating slope value, said variation to a predetermined limit, wherein said predetermined limit comprises a predetermined positive value in response to the differentiated cardiac signal having a positive slope and a predetermined negative value in response to the differentiated cardiac signal having a negative slope; and means for adjusting the discriminating slope value as a function of the collected cardiac signal.

19. The device of claim 18 wherein the predetermined positive value is equal to said predetermined negative value and equal to a fraction of said discriminating slope value.

20. The device of claim 18 further comprising means for adjusting said predetermined positive value and said predetermined negative value as a function of the collected cardiac signals.

21. An active implantable medical device comprising:

a detector to collect a cardiac signal, said collected cardiac signal comprising a characteristic signal component and a parasitic signal component, and a discriminating means for receiving as an input the collected cardiac signal and delivering as an output a signal corresponding essentially to the characteristic signal, wherein the discriminating means further comprises:

a differentiating and limiting means for differentiating the cardiac signals, evaluating the differentiated cardiac signal for variations in said cardiac signal relative to a discriminating slope value and determining whether the slope is positive or negative, and for limiting, in response to a variation being greater than said discriminating slope value, said variation to a predetermined limit, wherein said predetermined limit comprises a predetermined positive value in response to the differentiated cardiac signal having a positive slope and a predetermined negative value in response to the differentiated cardiac signal having a negative slope, wherein the predetermined positive value is equal to said predetermined negative value and equal to a fraction of said discriminating slope value; and means for adjusting the discriminating slope value as a function of the collected cardiac signal.

22. An active implantable medical device comprising:

a detector to collect a cardiac signal, said collected cardiac signal comprising a characteristic signal component and a parasitic signal component, and a discriminating means for receiving as an input the collected cardiac signal and delivering as an output a signal corresponding essentially to the characteristic signal, wherein the discriminating means further comprises:

a differentiating and limiting means for differentiating the cardiac signals, evaluating the differentiated cardiac signal for variations in said cardiac signal relative to a discriminating slope value and determining whether the slope is positive or negative, and for limiting, in response to a variation being greater than said discriminating slope value, said variation to a predetermined limit, wherein said predetermined limit comprises a predetermined positive value in response to the differentiated cardiac signal having a positive slope and a predetermined negative value in response to the differentiated cardiac signal having a negative slope, wherein the predetermined positive value is equal to said predetermined negative value and equal to a fraction of said discriminating slope value; and means for adjusting said predetermined positive value and said predetermined negative value as a function of the collected cardiac signals.

23. An active implantable medical device comprising:

a detector to collect a cardiac signal, said collected cardiac signal comprising a characteristic signal component and a parasitic signal component, and a discriminating means for receiving as an input the collected cardiac signal and delivering as an output a signal corresponding essentially to the characteristic signal, wherein the discriminating means further comprises:

a differentiating and limiting means for differentiating the cardiac signals, evaluating the differentiated cardiac signal for variations in said cardiac signal relative to a discriminating slope value and determining whether the slope is positive or negative, and for limiting, in response to a variation being greater than said discriminating slope value, said variation to a predetermined limit, wherein said predetermined limit comprises a predetermined positive value in response to the differentiated cardiac signal having a positive slope and a predetermined negative value in response to the differentiated cardiac signal having a negative slope; and means for adjusting the predetermined positive value and the predetermined negative value as a function of the collected cardiac signal.

24. The device of claim 23 wherein the predetermined positive value is equal to said predetermined negative value and equal to a fraction of said discriminating slope value.

* * * * *